United States Patent [19]
Seidner

[11] Patent Number: 4,463,458
[45] Date of Patent: Aug. 7, 1984

[54] INTRAOCULAR LENS AND IMPLANTATION METHOD

[75] Inventor: Steven Seidner, Redondo Beach, Calif.

[73] Assignee: Vision Laboratories Inc., New York, N.Y.

[21] Appl. No.: 439,998

[22] Filed: Nov. 8, 1982

[51] Int. Cl.$^3$ .......................... A61F 1/16; A61F 1/24
[52] U.S. Cl. ........................................................ 3/13
[58] Field of Search ......................................... 3/13, 1

[56] References Cited

U.S. PATENT DOCUMENTS

| | | |
|---|---|---|
| D. 175,269 | 8/1955 | Nelson . |
| 3,229,303 | 1/1966 | Jonassen . |
| 3,925,825 | 12/1975 | Richards et al. ........................ 3/13 |
| 3,975,779 | 8/1976 | Richards et al. ........................ 3/13 |
| 4,122,556 | 10/1978 | Poler ....................................... 3/13 |
| 4,159,546 | 7/1979 | Shearing ................................. 3/13 |
| 4,174,543 | 11/1979 | Kelman .................................. 3/13 |
| 4,249,271 | 2/1981 | Poler ....................................... 3/13 |
| 4,363,143 | 12/1982 | Callahan ................................. 3/13 |

FOREIGN PATENT DOCUMENTS 820823  4/1981  U.S.S.R. .................................. 3/13

OTHER PUBLICATIONS

"A Guide for Implantation of the Kelman Anterior Chamber Intraocular Lens", by Charles D. Kelman, Printed Courtesy of Heyer-Schulte Medical Optics Center, 1402 E. Alton Ave., Irvine, California 92714, pp. 1-12, Nov. 1980.

"The Lindstrom Centrex Lens", by Richard L. Lindstrom, Brochure, pp. 1-11, Copyright 1981.

Primary Examiner—Ronald L. Frinks
Attorney, Agent, or Firm—Amster, Rothstein & Engelberg

[57] ABSTRACT

The risk of surgical injury to the eye during implantation of an intraocular lens is reduced by pre-positioning either all or a major portion of the lens assembly in the anterior chamber of the eye prior to extraction of the cataract.

7 Claims, 5 Drawing Figures

INTRAOCULAR LENS AND IMPLANTATION METHOD

This invention relates to an improved method of removing a cataract or an otherwise diseased natural lens from the eye and to the replacement thereof with a novel intraocular lens structure.

The surgical procedures for removal of a cataract and the replacement of the clouded lens with a synthetic intraocular lens have been in use for many years. In the most common surgical procedure, a small incision is made at the top of the eye in the region of the limbus where the cornea meets the sclera. An intracapsular extraction, i.e., a procedure in which the entire lens and capsule is removed, or extracapsular extraction, i.e., a procedure in which the capsule is only partially removed, is then performed by extracting the lens, normally through the pupil with special forceps or a cryoprobe. Thereafter, the synthetic lens assembly is inserted through the incision and physically manipulated into place in either the anterior or posterior chamber by utilizing a suitable surgical instrument.

A large variety of intraocular lens structures are known in the art. A typical lens structure consists of a central optic section and one or more peripheral stabilizing feet or haptics as illustrated, for example, by Poler U.S. Pat. Nos. 4,122,556 and 4,249,271; the Kelman Anterior Chamber Intraocular Lens; or the Lindstrom Centrex Posterior Chamber Lens. Alternately, the haptics may be in the form of iris clips as illustrated in Richards U.S. Pat. Nos. 3,925,825 or 3,975,779. Irrespective of the particular structure or configuration, the lens assembly, as a unit, is inserted through the incision after removal of the cataract and physically manipulated so that the lens is centered over the pupil area. For an anterior chamber lens, the haptics rest against and are stabilized by the anterior angle, i.e., the angle formed by the cornea and the plane of the iris. Because the lens structure is not normally sutured or otherwise permanently anchored to the iris, except by the growth of tissue adjacent to the haptics, the size and arrangement of the haptics is crucially important in ensuring that the lens remains immobile after implantation. Accordingly, the use of structures having three feet spaced apart so as to define a stable plane is one popular overall haptic structure. It is also important that the overall diameter of the lens assembly closely approximate the diameter of the chamber or adjust to the diameter of the chamber in which the lens is implanted so as to minimize the opportunity for movement in any direction.

While the foregoing surgical method and lens implantation technique has been generally successful, it entails certain risks. More specifically, as a result of the surgical procedures which are required to remove the cataract, the eye loses some of its structural integrity and rigidity; the vitreous humor is exposed; and the aqueous humor flows into the void left by the removal of the lens. Since cataract surgery is commonly performed on elderly people who may have a weaker vitreous membrane and a more watery vitreous humor, a risk exists that the vitreous will be punctured either by the lens assembly or the lens insertion instrument when the lens assembly is physically manipulated into position, thereby permanently impairing the patient's vision. Further, because the iris is soft and floppy after the lens extraction, it may adhere to the intraocular lens assembly during the manipulations required to position the lens, thereby causing folds or tucks to develop in the iris which will distort the pupil.

It is an object of the present invention to provide a novel surgical procedure for cataract removal and lens implantation which reduces the risk of surgical injury to the eye.

Another object of the invention is to provide a novel intraocular lens structure which is easier to insert and position in the eye and which reduces the possibility of surgical injury during implantation.

It has now been discovered that intraocular lens implantation can be simplified and improved by employing a novel method and lens assembly which together permit all or a substantial portion of the lens assembly to be pre-positioned in the anterior chamber of the eye prior to removal of the cataract. More specifically, in the novel method of the invention, the surgical procedure commences with a normal incision, but thereafter, and prior to the removal of the cataract, at least a portion of a lens assembly is inserted through the incision and physically manipulated so that at least one and as many as all of the stabilizing feet or haptics associated with the lens assembly are pre-positioned in the anterior chamber of the eye at substantially the location which they will permanently occupy when the surgical procedure is completed and the lens assembly is functioning as a replacement for the surgically removed cataract. The cataract is then surgically removed in accordance with any of the prior art surgical techniques. Surgical removal is possible without interference from the pre-positioned lens assembly because the optic or lens portion thereof is either not placed in its final position or is temporarily movable therefrom and, accordingly, will not interfere with the normal physical manipulations which occur during the step of surgically removing the cataract. Following extraction of the cataract, the optic section of the lens assembly is either placed in or, by virtue of its resilient structure, automatically moves into its final position with respect to the pre-positioned portion of the lens assembly, and the incision is sutured to complete the operation.

The novel method of the invention is made possible by employing novel intraocular lens structures. In one embodiment, such lens structure comprises a two-piece assembly consisting of a frame section and an optic section. The frame section is adapted to receive the optic section and includes one or more peripheral stabilizing feet or haptics. The separate optic section is adapted to clip on to or otherwise mate with the frame section and includes a lens and one or more additional peripheral stabilizing feet or haptics. When this embodiment of the invention is employed, only the frame section of the two-piece lens assembly is inserted through the incision and physically manipulated so that the haptics associated therewith are placed into their respective proper final locations in the anterior chamber of the eye prior to surgical removal of the cataract. The optic section of the lens assembly is inserted through the incision and slipped into mating engagement with the pre-positioned frame section after surgical removal of the cataract.

In an alternative embodiment of the invention, the lens assembly consists of integral frame and optic sections, but the lens assembly is so constructed that it may be partially or totally rotated, folded, or otherwise moved to a position which will not interfere with the surgical removal procedure and thereafter readily moved into its final position. In this embodiment, the entire lens assembly is inserted in the eye prior to surgical removal of the cataract; at least some, if not all, of the haptics associated with the lens assembly are pre-positioned; and the optic section is folded, rotated, or otherwise moved to a position where it will not be an obstacle to the normal surgical procedure. Preferably, the optic section is moved in a manner complementary with the cornea which must also be partially folded, rolled back or lifted to expose the cataract for surgical removal. The optic section will, of course, be returned to a pre-determined location in relation to the pre-positioned frame section of the lens assembly following the cataract removal so that it may function as a replacement for the surgically removed lens.

It will be readily apparent that the foregoing procedure and lens structure significantly reduces the risk of surgical eye injury since either all or a substantial portion of the physical manipulations required to position the intraocular lens within the anterior chamber will occur before surgical removal of the lens. Further, because the lens assembly has either an open or movable central section and is pre-positioned by the proper placement of the haptics associated with the lens assembly in the peripheral portion of the eye, the pre-positioning of the lens assembly or at least a major portion thereof in the eye does not interfere with the surgical procedures required to thereafter remove the natural lens.

The foregoing and further features of the invention will become further apparent from the following more detailed specification and accompanying drawings of some of the possible designs in which.

Figure 1:
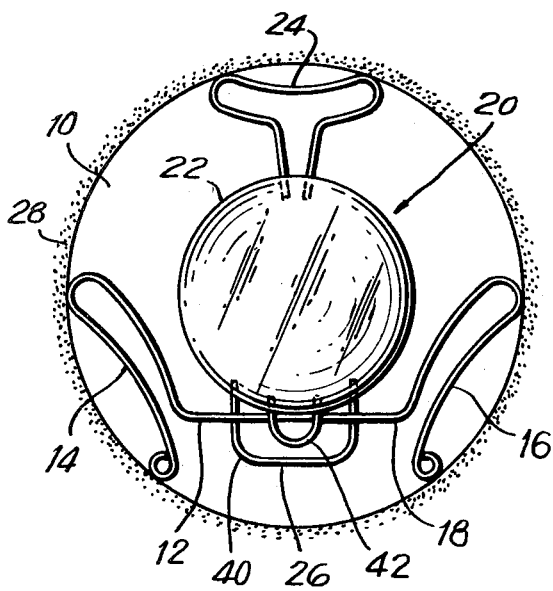
FIG. 1 is a frontal view of one embodiment of an assembled two-piece lens structure positioned in the eye.
Figure 2:
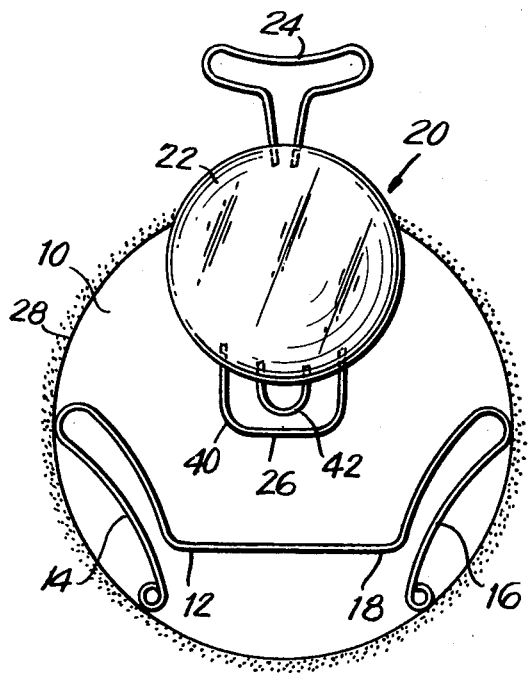
FIG. 2 is an exploded frontal view of the embodiment of FIG. 1.

Referring to the drawings, FIGS. 1 and 2 illustrate one embodiment of a lens assembly 10 in accordance with the invention for achieving mating engagement between a frame section and an optic section. This embodiment includes a frame section 12 comprising haptics 14 and 16 joined by intermediate optic receiving member 18 and an optic section 20 comprising a lens 22, haptic 24 and clip means 26. As illustrated, the frame section and haptics are made of thin flexible wire-like plastic or other biologically inert materials which exhibit some degree of resilience and are capable of being bent or otherwise manipulated so as to be properly located within the eye. Indeed, the structure and materials of the haptic sections are usually selected to enable a degree of size adjustment so that the normal inventory of lens assemblies for different eye sizes can be significantly reduced.

As best seen in FIG. 1, the overall diameter of the frame section 12 is selected so as to be approximately the same diameter as the anterior chamber of the eye 28, so that the frame section will not be able to undergo significant movement after it has been properly located in the anterior chamber. It will be readily apparent to those skilled in the art that a frame section of appropriate size must be selected for each patient based upon careful measurement of the diameter of the anterior chamber of the eye in accordance with well-established measuring techniques. However, as previously noted, the haptics 14, 16 and 24 may be made of materials which permit some size adjustment.

It will also be apparent that while the specific shape of the haptics is not critical, at least a portion of each haptic will be arranged to extend to the outermost periphery of the anterior chamber in order to maximize the stability of the frame once it is positioned within the eye and to limit the ability of the frame to undergo any significant movement. In one preferred embodiment, the haptics will also all be in substantially the same plane to further enhance stability.

Figure 4:
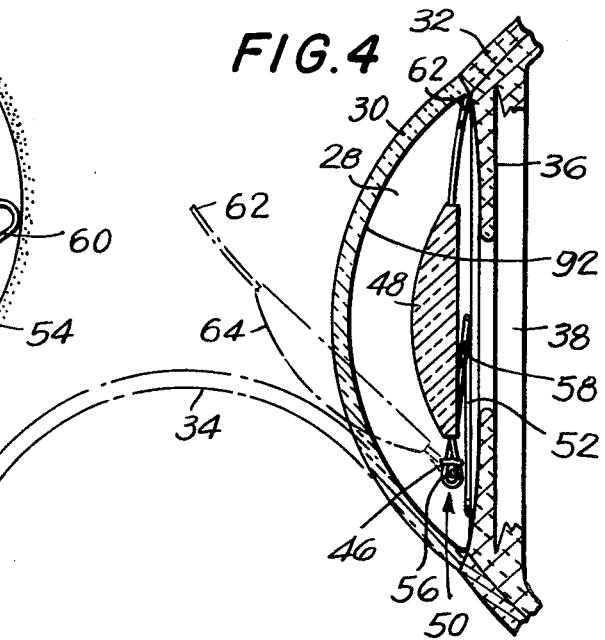
FIG. 4 is a sectional view taken at 4—4 of FIG. 3.

The lens assembly 10 as defined above is inserted in the eye in the following manner. As best seen in FIG. 4, an incision is made in the limbal region of the eye where the cornea 30 joins the sclera 32. The cornea is thereafter peeled back, as shown by the exaggerated shadow line 34 in FIG. 4, to expose the interior of the eye. Frame section 12 of the lens assembly 10 is thereafter inserted in the anterior chamber 28 and positioned in the lowermost portion of the eye so that the haptics 14 and 16 either abut the angle formed by the junction of the cornea 30 and iris 36 at the outer periphery of the anterior chamber 28, or are in close proximity thereto. Once in position, the frame section will also rest in the anterior angle.

After the frame section of the lens assembly is in position, the natural lens of the eye, which is not shown in the drawing but is positioned in the posterior chamber 38, is surgically removed by any of the known prior art techniques. Following extraction of the cataract, the optic section 20 is inserted and mated with the frame section. More particularly, clip 26 of the optic section 20, which consists of legs 40 and 42, engages intermediate member 18 of the frame section, and the haptic 24 associated with optic section 20 is positioned to form a third stabilization point at the outer periphery of the anterior chamber 28. It will be understood that the clip 26 is intended to be illustrative of one mechanism for uniting the frame and optic sections of the lens assembly and that many other mechanical configurations will readily occur to those persons of ordinary skill in the art.

The lens assembly will, of course, be formed from materials which are biologically inert, i.e., are not susceptible to being absorbed by body fluids and are capable of being well tolerated by the human body when implanted. A wide variety of plastics are capable of meeting the foregoing criteria, including polymethylmethacrylate and polypropylene. In addition, lens 22 must be capable of exhibiting the necessary optical characteristics, and may be formed of ophthalmic glass, quartz, methacrylate resins or similar materials.

It will be readily appreciated by those skilled in the art that, for illustrative purposes, the haptics 14, 16 and 24 are shown as actually abutting the peripheral edge of the anterior chamber. In actual practice, a perfect fit may not be achieved and there may be a slight gap between one or more of the haptics and the angle defining the outermost periphery of the anterior chamber. It will also be appreciated that the overall size and shape of the frame section 12 and optic section 20 of the lens assembly including, for example, the length of the frame legs; the angle at which they extend and the number and shape of the haptics may vary widely without departing from the intent of the invention. Irrespective of the specific configuration, the frame section will be designed and arranged to establish a stable position in the anterior chamber at the lowest feasible point so as to minimize any possibility that the placement of the frame section prior to extraction of the cataract will interfere with the extraction procedure. The optic section, irrespective of its particular configuration, will be adapted to mate with the frame section in a manner which will limit its movement after it is finally positioned, and will be of an overall size sufficient to ensure that the haptics associated with the optic section extends upwardly a sufficient distance to ensure that at least a portion of the haptic is substantially co-extensive with the angle defining the outer periphery of the anterior chamber.

Figure 3:
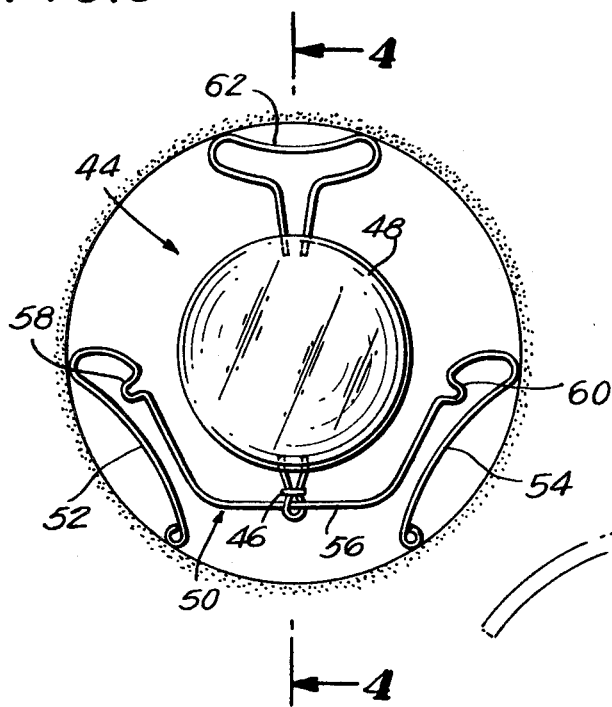
FIG. 3 is an alternative embodiment illustrating a one-piece lens structure suitable for pre-positioning in the eye.

FIGS. 3 and 4 illustrate a further embodiment of the invention which comprises a lens assembly having integral frame and optic sections but including structure which permits the optic section to be movable so that it will not interfere with the physical space required for surgical removal of the cataract. The lens assembly 44 depicted in FIG. 3 is quite similar to that shown in FIGS. 1 and 2 except that the clip 26 appended to the optic section 20 has been replaced by an integral hinge 46 connected to optic section 48. The lens assembly also includes a frame section 50 composed of haptics 52 and 54 and intermediate member 56 around which hinge 46 is permitted to pivot. As illustrated, haptics 52 and 54 include loops 58 and 60 which provide these members with a degree of size adjustability. A similar loop could be included in haptic 62 associated with the optic section.

As with the other embodiments of the invention, the lens assembly of FIG. 3 is inserted into the eye after the incision is made in the limbal region between the cornea 30 and sclera 32. However, unlike the other embodiments the entire lens assembly including both the frame section 50 and integral optic section 48 is pre-positioned prior to extraction of the cataract. More particularly, the haptics 52 and 54 are pre-positioned in the lowermost portion of the anterior chamber of the eye as previously described in connection with the other embodiments. However, prior to extracting the cataract, the cornea 30 is folded back (as illustrated by the shadow line 34 in FIG. 4) to provide operating space for the surgical procedure, and the optic section 48 is rotated about hinge 46 so that it too is removed from the operating field to a position such as shown by outline lens 64. Upon completion of the cataract extraction, the optic section 48 is rotated back into a position where its lens can function as a replacement for the removed cataractus lens, and the haptic 62 associated with the optic section 48 is manipulated into its final position as shown in FIG. 3.

Figure 5:
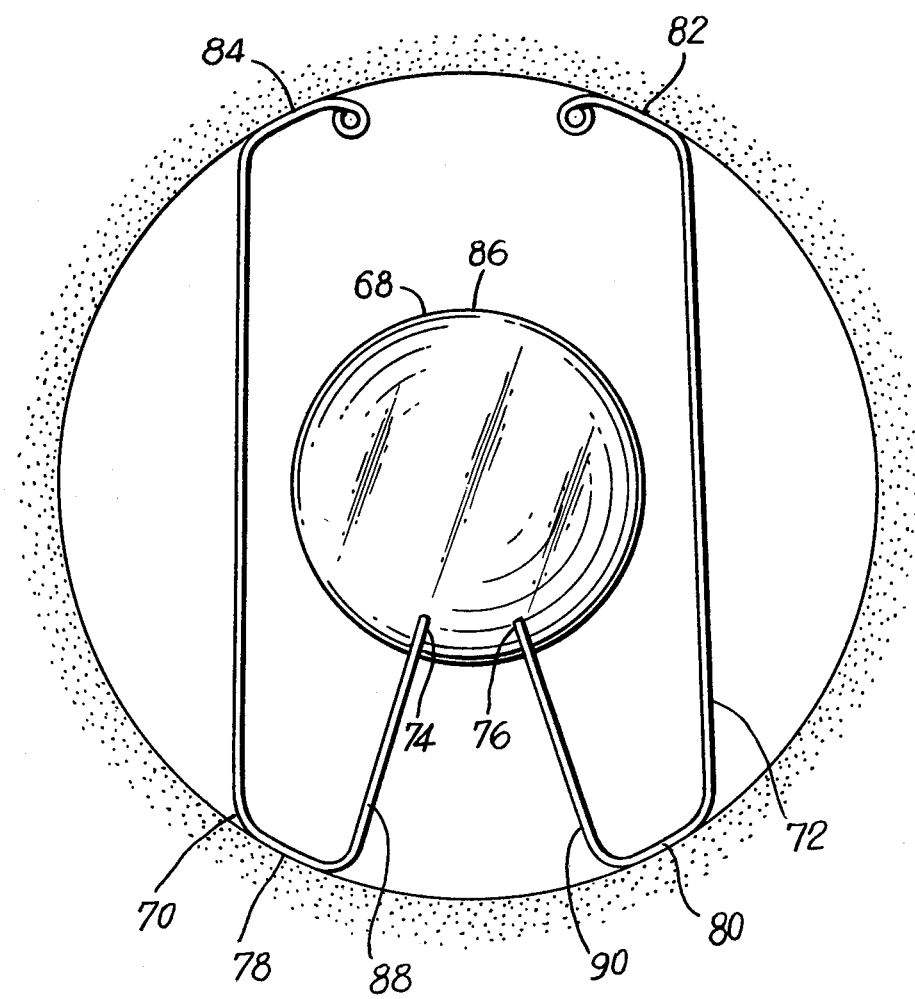
FIG. 5 is a further alternative embodiment illustrating another form of a one-piece lens structure suitable for pre-placement in the eye in connection with cataract surgery.

It will be readily apparent that the hinge 46 is merely illustrative of one mechanical embodiment of an integral but movable optic section and that many other mechanical configurations could be used. FIG. 5 illustrates one such preferred embodiment which is based on the principle of a "live" hinge which exhibits elastic memory. More particularly, there is illustrated a lens assembly 66 comprising an optic section 68 and a frame section consisting of haptics 70 and 72. As illustrated, the haptics are permanently joined to the optic section at points 74 and 76. As in the other embodiments, the haptics are made of biologically inert materials which exhibit a degree of resiliency and are so constructed and arranged so that the overall diameter of the lens assembly 66 closely approximates the diameter of the anterior chamber of the eye. The stability of lens assembly 66 is maintained by the fact that haptics 70 and 72 provide four contact points 78, 80, 82 and 84 at the outermost periphery of the anterior chamber which all preferably lie in substantially the same plane.

It will be readily apparent that the end 86 of optic section 68 opposite to the points 74 and 76 where the haptics are joined to the optic section is unrestrained. Accordingly, in use, the lens assembly 66 of FIG. 5 will be pre-placed in precisely the same fashion described with respect to the lens assembly 44 of FIGS. 3 and 4, except that all of the haptics will be pre-placed in their final positions before the cataract is removed. The unrestrained end 86 of optic section 68, the junction points 74 and 76, which preferably are located within less than 180° from each other and the periphery of the optic section, either alone or acting together with legs 88 and 90, respectively, of haptics 70 and 72, will function like a live hinge having elastic memory. Thus, during surgery, the optic section will readily move out of the surgical field, e.g., to a position similar to optic section 48 in FIG. 4, in response to any force applied on or near its free end 86 by the surgeon-surgical instruments or by contact with the natural lens as it is being extracted, but it will automatically return to its pre-positioned location as a replacement lens as a result of elastic memory when the force applied is released.

It will be understood by those skilled in the art that the mechanical arrangement for achieving a live hinge shown in FIG. 5 is illustrative only, and that a wide variety of arrangements which are functionally equivalent thereto will be readily apparent.

It will also be apparent that care must be taken to avoid damaging the inner surface of the cornea or endothelium 92 as a result of contact with the optic section of the lens during the surgery. Accordingly, the preferred embodiment of the invention contemplates the use of a coating on either the endothelium, the optic section or both to reduce friction and the possibility of injury. In one contemplated embodiment, a hydrophilic polymer coating, e.g., a hydroxyethyl methacrylate coating, is grafted or otherwise applied to the lens and other optic section surfaces for that purpose. Other temporary or permanent liquid or solid coatings having the appropriate physical properties could also be employed.

What is claimed is:

1. A method of implanting an intraocular lens which comprises, making a surgical incision in the eye, inserting at least a portion of an intraocular lens assembly in the anterior chamber of the eye, pre-positioning at least one haptic associated with said lens assembly so that it is located at substantially the final position in said anterior chamber which it will occupy when the optic section of said lens assembly is in a position to function as a replacement for a surgically removed natural lens of the eye or portion thereof, and thereafter surgically removing at least a portion of said natural lens.

2. The method of claim 1, wherein the entire intraocular lens assembly is inserted in said anterior chamber prior to said surgical removal step.

3. The method of claim 1, wherein all of the haptics associated with said lens assembly are pre-positioned at substantially said final position in said anterior chamber.

4. The method of claim 1, wherein said lens assembly comprises a frame section and a separate optic section, said frame section and the haptics associated therewith are pre-positioned in said anterior chamber prior to said surgical removal step and said optic section is inserted into said frame section following said surgical removal step.

5. The method of claim 1, wherein said lens assembly comprises a frame section, an optic section and a hinge integrally connecting said frame section and said optic section, the entire intraocular lens assembly is inserted into the anterior chamber of the eye prior to said surgical removal step and said optic section is first moved about said hinge, subsequent to said pre-positioning step, to a location where it does not interfere with said surgical removal step and finally moved about said hinge to a position where it can function as a replacement for the surgically removed natural lens.

6. The method of claim 5, wherein all of the haptics associated with said lens assembly are pre-positioned at substantially said final position in said anterior chamber prior to said surgical removal step.

7. The method of claim 6, wherein said hinge has elastic memory and said first movement of said optic section about said hinge is in response to a force applied to said optic section and said final movement is in response to said elastic memory of said hinge.

* * * * *